United States Patent [19]

Johan et al.

[11] Patent Number: 5,078,508
[45] Date of Patent: Jan. 7, 1992

[54] DISPOSABLE BAG FOR CONTAMINATED MEDICAL WASTE

[76] Inventors: Tom Johan, 9921 Carmel Mountain Rd., No. 116, San Diego, Calif. 92129; Robert Johan, 4644 Blue Jay St., Orange, Calif. 92669

[21] Appl. No.: 684,997

[22] Filed: Apr. 15, 1991

[51] Int. Cl.$^5$ ................. B65D 30/08; B65D 33/28
[52] U.S. Cl. ............................. 383/75; 383/109
[58] Field of Search ........... 383/119, 75, 109, 110; 229/87.11; 206/523

[56] References Cited

U.S. PATENT DOCUMENTS

| | | | |
|---|---|---|---|
| 1,942,917 | 1/1934 | D'Este et al. | 383/110 |
| 3,204,825 | 9/1965 | Underwood | 383/109 |
| 3,283,994 | 11/1966 | Miller | 383/75 |
| 3,494,457 | 2/1970 | Titchenal | 383/109 |
| 3,948,436 | 4/1976 | Bambara | 383/119 |
| 4,356,221 | 10/1982 | Anthony et al. | 383/109 |
| 4,533,578 | 8/1985 | Boyd et al. | 383/119 |
| 4,815,590 | 3/1989 | Peppiatt | 383/119 |
| 4,857,042 | 8/1989 | Schneider | 383/109 |
| 4,890,936 | 1/1990 | Cooper | 383/109 |

FOREIGN PATENT DOCUMENTS 2163724 3/1986 United Kingdom .............. 383/110

Primary Examiner—Stephen P. Garbe

[57] ABSTRACT

A multi-ply bag is provided which is especially constructed for the disposal of medical waste. The bag comprises an inner ply formed of a strong impervious plastic material, such as polyurethane, which is resistant to tearing by sharp objects; an intermediate ply of fabric materials, such as cotton, which is capable of absorbing liquid medical waste; and an outer ply formed of strong impervious plastic material, which likewise may be polyurethane; the outer ply extending beyond the upper edges of the inner and intermediate plies and has a sleeve formed around its upper edge for receiving a drawstring.

5 Claims, 1 Drawing Sheet

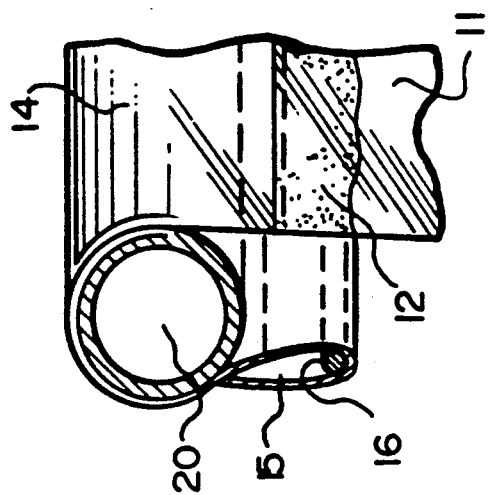
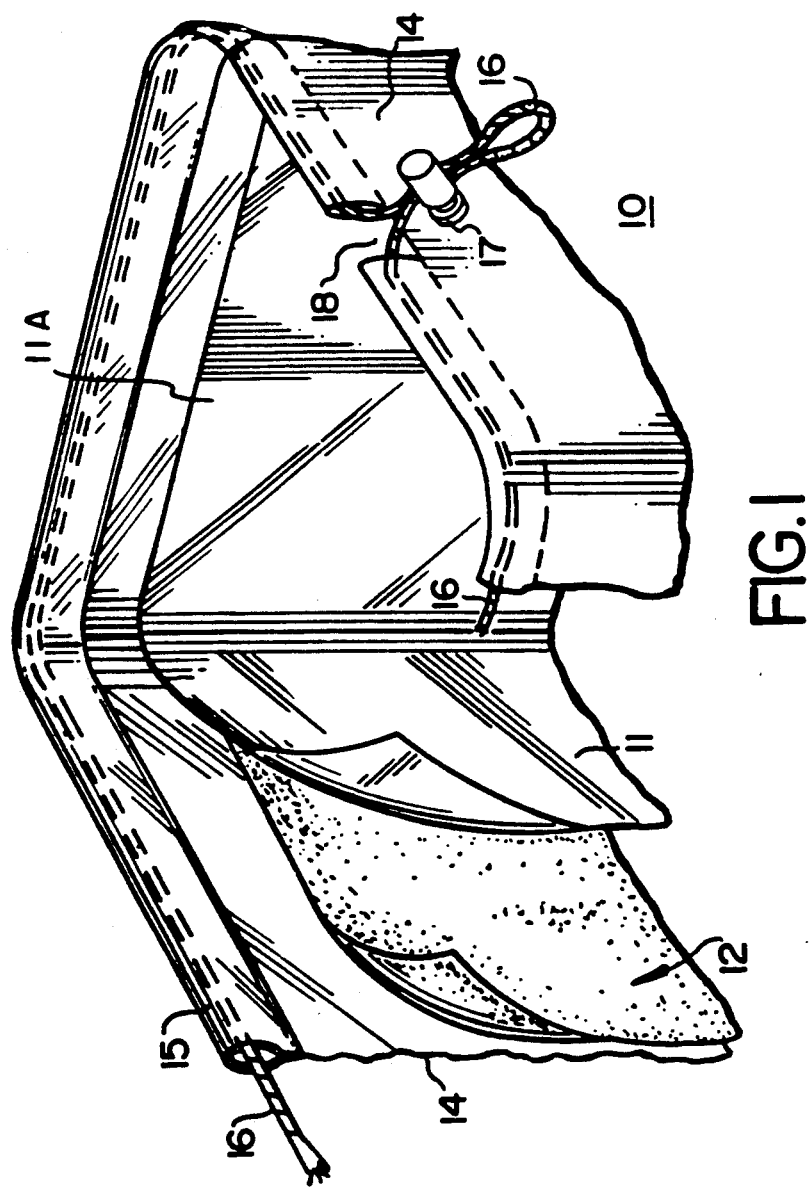

DISPOSABLE BAG FOR CONTAMINATED MEDICAL WASTE

BACKGROUND OF THE INVENTION

The efficient and safe disposal of contaminated medical waste has long been a problem. It has been usual in the past to provide collapsible racks which support plastic bags into which the waste may be deposited. However, medical waste often contains sharp objects which tend to tear the prior art bags. This results in the liquid medical waste spilling through the tears, even though the solid waste may still be retained in the bag, which is often not the case.

SUMMARY OF THE INVENTION

The present invention provides a bag for receiving medical waste which is particularly constructed to overcome the deficiencies of the prior art bags. The bag of the invention has a multi-ply construction, and it comprises an inner ply formed of a strong impervious plastic material, such as polyurethane, which is resistant to tearing by sharp objects; an intermediate ply formed of fabric material, such as cotton, which is capable of absorbing liquid material in the event tearing does occur in the inner ply; and an outer ply which may be formed of the same impervious strong plastic material as the inner ply, and which insures that no liquid medical waste will escape from the bag. The likelihood of sharp objects in the bag tearing through both the inner and outer plys is minimal for all practical purposes.

BRIEF DESCRIPTION OF THE DRAWING

FIGURE 1 is a perspective view of a multi-ply waste disposal bag incorporating the concepts of the invention, the view being of the upper portion of the bag, and being broken away to reveal the various plys which make up the bag; and FIG. 2 is a partial fragmentary view showing the manner in which the upper edge of the bag of FIG. 1 may be wrapped around an upper bar of a bar hamper of the type disclosed, for example, in Copending Application Serial No. 07/684,988, filed Apr. 15, 1991, in the name of the present inventors, to cause the bag to be securely held on the hamper in the open condition of FIGURE 1.

DETAILED DESCRIPTION OF THE ILLUSTRATED EMBODIMENT

As shown in FIGURE 1, the bag 10 of the present invention comprises an inner, tear resistant ply 11 formed of a strong impervious plastic material such as polyurethane, and which may be of the order of 2 mils thick. The bag also comprises an absorbing intermediate ply 12 which may be formed, for example, of cotton, or equivalent fabric material. Ply 12 may be treated to be disinfecting and deodorizing. Finally, the bag also comprises an outer ply 14 which may be of the same impervious and strong plastic material as the inner ply, and which may have the same thickness as the inner ply.

As shown in FIGURE 1 for example, the outer ply 14 extends upwardly from the upper edges of the intermediate ply 12 and inner ply 14, and a sleeve 15 is formed around the upper edge of the outer ply 14. A drawstring 16 is threaded through the sleeve 15 for closing the bag. The ends of the drawstring extend through a cut-out 18, and through a buckle 17. The buckle 17 may be of the usual spring-loaded type, and it may be actuated to permit the drawstring to be drawn tight to close the bag. Then, when released, the buckle clamps onto the drawstring to hold the bag in its closed condition. The upper edge of the inner ply extends beyond the upper edge of the intermediate ply 12, and the outer ply 14 is heat sealed to the upper edge of the inner ply 11, or otherwise adhesively attached to the inner ply.

As shown in FIG. 2, the upper edge of the outer ply 14 may be wrapped around the upper bar 20 of a hamper of the type described in the Copending Application referred to above. Then, when the drawstring 16 is pulled tight, and the buckle 17 released, the waste bag is securely mounted on the hamper in an open position for receiving medical waste.

The invention provides, therefore, an improved and simple multi-ply bag for the disposal of medical waste, and the like, including toxic liquids and sharp objects. The bag assures that no toxic liquids or solids will escape, in the event of tearing. The bag is easy to use, and it may be securely mounted on the top of a supporting hamper, as described above.

It will be appreciated that while a particular embodiment of the invention has been shown and described, modifications may be made. It is intended in the claims to cover all modifications which come within the true spirit and scope of the invention.

I claim:

1. A bag for contaminated medical waste, and the like, comprising: an inner-ply formed of a strong impervious plastic material resistant to being torn by sharp objects; and an outer-ply formed of an strong impervious plastic material likewise resistant to being torn by sharp objects; the upper end of the outer-ply extending beyond the upper edge of the inner ply, and said inner and outer plys being sealed to one another adjacent to the upper edges thereof.

2. The bag defined in claim 1, and which includes an intermediate ply supported between the inner and outer plys, and formed of a liquid absorbent fabric materials.

3. The bag defined in claim 2, in which said inner ply is composed of a polyurethane plastic material, said intermediate ply is formed of cotton, and said outer ply is also composed of a polyurethane plastic material.

4. The bag defined in claim 1, and which includes a sleeve formed in the upper end of the outer ply around the upper edge thereof, for receiving a drawstring.

5. The bag defined in claim 1, in which said inner and outer plys each has a thickness of the order of 2 mils.

* * * * *